United States Patent [19]
Gelfand

[11] 3,943,983
[45] Mar. 16, 1976

[54] MOISTURE SENSING SYSTEMS FOR ELECTRICALLY OPERATED LIQUID-HANDLING DEVICES

[75] Inventor: Daniel Gelfand, Cliffside Park, N.J.

[73] Assignee: Buchler Instruments, Div. of Searle Analytic, Inc., Fort Lee, N.J.

[22] Filed: May 23, 1974

[21] Appl. No.: 472,901

[52] U.S. Cl. ............... 141/192; 137/312; 141/130; 200/61.04
[51] Int. Cl.$^2$ ......................................... B65B 57/16
[58] Field of Search ................................. 137/312; 141/86–88, 130, 198, 192; 200/61.04, 61.06, 61.08; 340/235, 242, 244 R, 303

[56] References Cited
UNITED STATES PATENTS

| | | | |
|---|---|---|---|
| 1,174,827 | 3/1916 | Conway | 200/61.04 |
| 2,482,448 | 9/1949 | Wiest | 200/61.04 |
| 2,531,159 | 11/1950 | Rowell | 137/312 X |
| 3,205,921 | 9/1965 | Packard et al. | 141/130 X |

*Primary Examiner*—Richard E. Aegerter
*Assistant Examiner*—Frederick R. Schmidt
*Attorney, Agent, or Firm*—Karl F. Ross; Herbert Dubno

[57] ABSTRACT

A fraction collector or other electrically operated liquid-handling device has a tray underlying the device for collecting spilled liquid. A pitched surface in the tray gathers any spilled liquid into the vicinity of a sensor having a moisture-destructible or sensitive element which holds a switch against the force of a spring in a closed-circuit position, allowing power to be fed from a current source to the electrically operated device. Upon wetting and destruction of the element the spring is relieved to open the switch, thereby cutting off the power and stopping the operation of the liquid-handling device.

4 Claims, 6 Drawing Figures

MOISTURE SENSING SYSTEMS FOR ELECTRICALLY OPERATED LIQUID-HANDLING DEVICES

FIELD OF THE INVENTION

The present invention relates to electrically operated liquid-handling devices and more particularly to fraction collectors provided with moisture detectors for interrupting operations in the event of spillage.

BACKGROUND OF THE INVENTION

Fraction collectors and other electrical devices which handle liquids have the inherent disadvantage in that they have to be watched carefully during their operation for spills (e.g. from misalignment of a tube with the outlet, from failure of the liquid metering means, from omission of a tube of a collecting array, etc.) which in some cases could be dangerous and expensive and at the very least requires the attention of someone who could be doing more productive work.

OBJECTS OF THE INVENTION

It is therefore an object of the invention to provide an improved fraction collector which will cease operation in the event of liquid spillage.

It is another object of the invention to provide a device which can be used with any electrically operated liquid-handling apparatus for detecting and shutting down operations when spillage occurs.

It is a further object of the invention to provide a system for detecting liquid spills which will not require the attention of an operator.

SUMMARY OF THE INVENTION

The above and other objects of the invention are realized in a fraction collector of the type having a base upon which is supported a number of collecting tubes arranged in rows held by racks which can be engaged by a drive mechanism for advancing the tubes to and from a filling position beneath a reservoir which is provided with a solenoid valve arrangement for metering a liquid in a predetermined amount into each of the tubes from the reservoir.

In the base of the fraction collector there is provided a tray for collecting stray liquid which has been spilled by either misalignment of a tube with the metering arrangement or splashing from a filled tube. The tray has a pitched surface for gathering the stray liquid into the vicinity of a moisture detector having a moisture-destructible element which holds a switch in a closed circuit position against the force of a spring acting to draw the switch into an open circuit position, the switch being connected in series with the solenoid valve and tube drive and a source of current.

The moisture-destructible element can be in the form of a tube made from filter paper which is highly absorbent to moisture and upon wetting, will weaken and collapse under the force of the spring which the element bears against to keep the switch in a closed circuit position and the fraction collector operating.

An alternative moisture-destructible element can have a strip of filter paper anchored at one end and engaging the switch with the other end into a closed-circuit position against the force of the aforementioned spring.

The collecting tray can be somewhat altered to form a different embodiment in which the tray is provided with an overlying perforated cover for supporting a vessel for any electrically operated liquid-handling device which can draw power from a number of outlets provided on the tray and connected through the moisture detector with a source of electric current.

Another moisture detector can have a pair of electrodes in contact with a filter paper element and connected with a circuit responsive to the change of conductivity of the paper when wetted, there being means operable by this circuit for interrupting the operation of any device in which the detector is included.

BRIEF DESCRIPTION OF THE DRAWING

The above and other features of the invention will now be described in detail with reference to the drawing in which.

SPECIFIC DESCRIPTION

Figure 1:
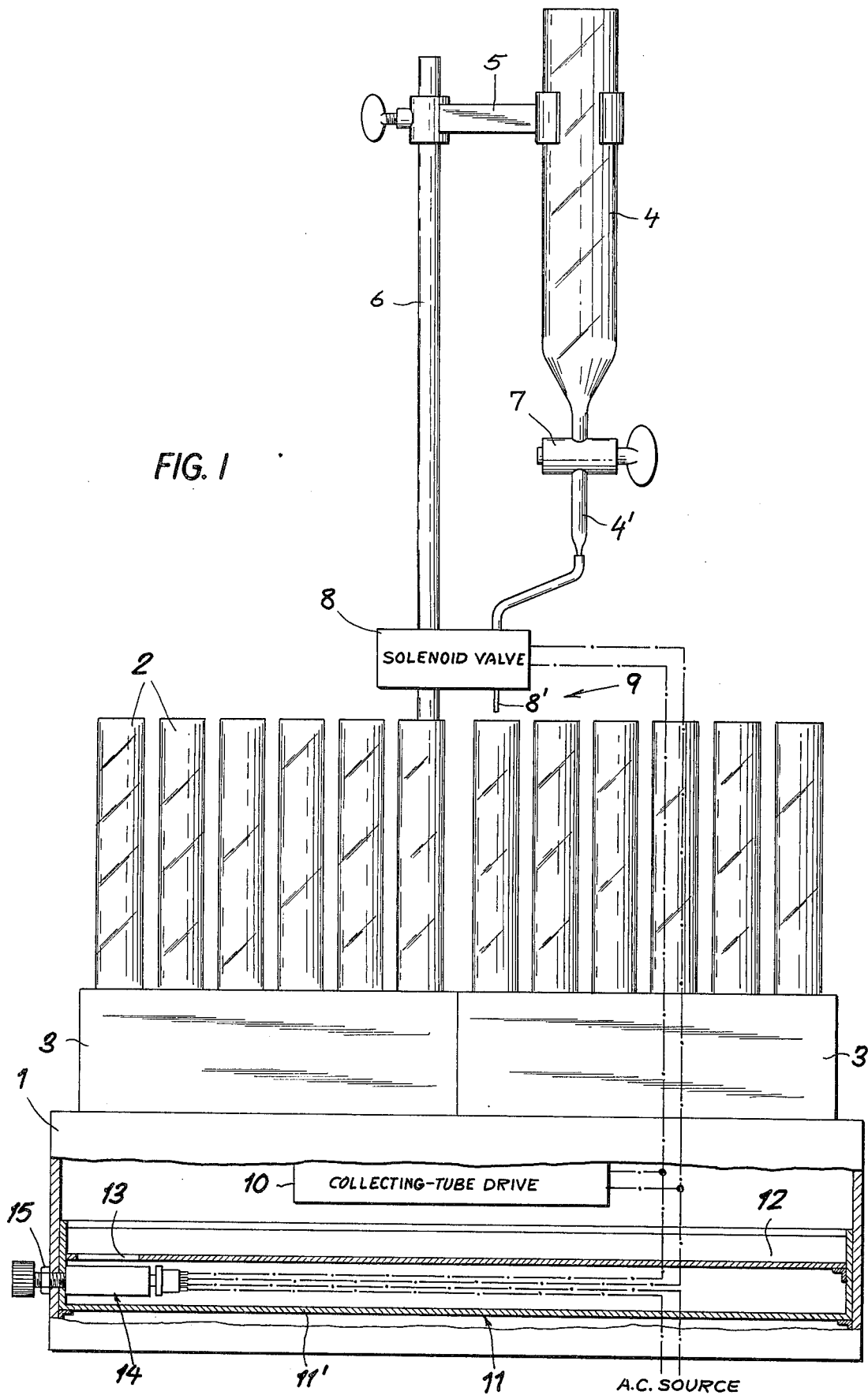
FIG. 1 is an elevational view with parts broken away of a fraction collector according to the invention.

The fraction collector shown in FIG. 1 has a base 1 upon which is supported a plurality of vessels in the form of collecting tubes 2 held in rows of six tubes each by racks 3. (See U.S. Pat. No. 3,221,781).

A source of liquid is provided above the tubes 2 in a reservoir 4 held in a clamp 5 supported on a standard 6 mounted on the base 1. The reservoir 4 has a small diameter passageway 4' provided with a stopcock 7 for feeding a liquid from the reservoir to a solenoid valve 8 which meters a predetermined amount of liquid into each collecting tube 2, as that tube is advanced to a filling position 9, beneath the valve output spigot 8' by a collecting tube drive 10.

Figure 2A:
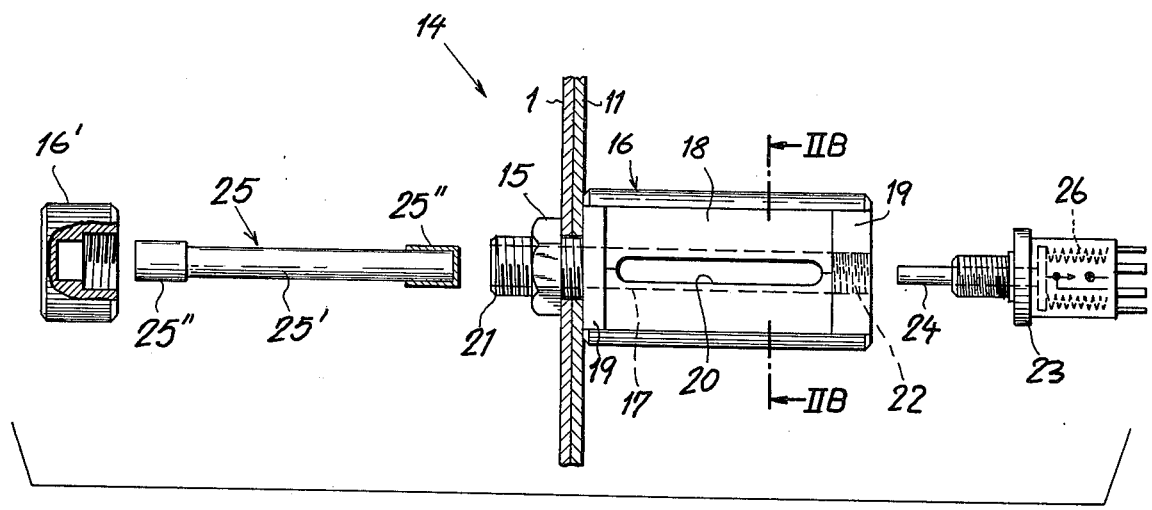
FIG. 2A is an exploded view of one embodiment of the invention.
Figure 2B:
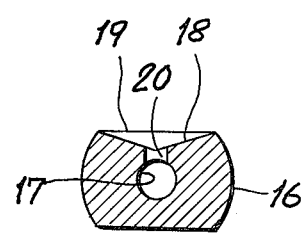
FIG. 2B is a sectional view taken along line IIB — 11B of FIG. 2A.

A tray 11 for collecting stray or spilled liquids from the valve 8 and tubes 2 is provided in the base 1, beneath the collecting tube array. The tray 11 has a pitched surface 12 for collecting and gathering the stray liquids in a particular area at which a cutout 13 is provided for feeding the collected liquid to a liquid-detector 14 located in a channel 11' beneath the cutout 13 and shown in more detail in FIGS. 2A and 2B.

The liquid-detector 14 is held in place beneath the output 13 by a nut 15 threaded onto an extension 21 passing through a side wall of base 1 and comprises a main body 16 having a central throughgoing bore 17. The upwardly facing portion of the body 16 is provided with a pitched surface 18 flanked at its ends by walls 19 and feeding into a slot 20 which communicates with the bore 17.

An externally threaded extension 21 through which the bore 17 passes is provided at one end of the body 16. The other end of bore 17 is internally threaded at 22 and engageable by a switch 23 having a plunger 24 which extends into the bore 17 and is in turn engageable by a moisture-destructible element 25 residing and held in place within bore 17 by an internally threaded end-piece 16' engageable with the extension 21.

The element 25 engages the plunger 24 into a closed switch position against the force of springs 26 which bias the switch 23 into an open circuit position when the moisture-destructible element 25, which is made up of filter paper formed into a tube 25' with end pieces 25", is wetted, causing the tube 25' to collapse under the force of springs 26.

The switch 23, is in series with a circuit supplying power to the collecting tube drive 10 and the solenoid valve 8 so that the failure of element 25 due to spillage causes the complete shutdown of the entire fraction collector.

After detection of spillage and the resultant shutdown of operations, the destroyed element 25 can be replaced by removing the endpiece 16' at the side of the base for access to the element.

Figure 3A:
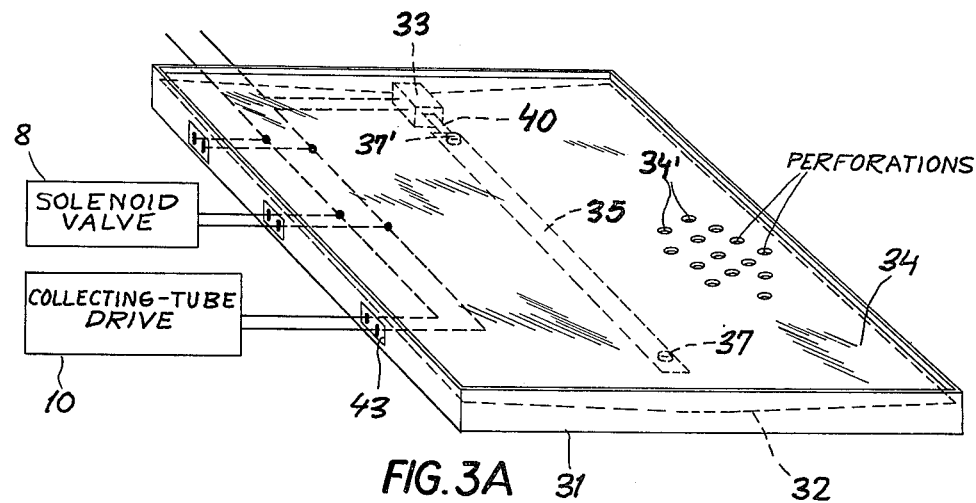
FIG. 3A is a perspective view of another embodiment of the invention.

The tray 31 shown in FIG. 3A is similar to the tray 11 and is provided with a pitched surface 32 which is removable from tray 31. A number of electrical outlets, in this case three outlets 43, are provided along one side of tray 31 for supplying power to electrically operated devices handling liquids which are prone to spillage.

A supporting surface 34 overlies the tray 31 and is provided with a number of perforations 34' for passing spilled liquid from liquid handling devices supported on the surface 34 to the pitched surface 32 where the liquid collects at the bottom of the pitch.

Figure 3B:
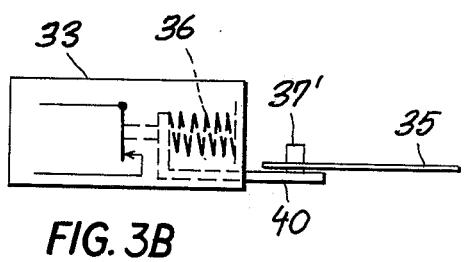
FIG. 3B is a view of an element of the embodiment shown in FIG. 3A.

Located at the bottom of the pitch is a moisture-destructible element 35 consisting of an elongated strip of filter paper anchored at one end to the surface 32 by a pin 37 provided thereon and passing through an eyelet provided in the strip. The other end of the strip 35 engages a pin 37' provided on the plunger 40 of switch 33, as shown in FIG. 3B, against the force of a spring 36 which biases the switch 33 into an open circuit position.

Upon wetting of the element 35 by any collected liquid, the force of spring 36 tears the moisture-weakened element apart and the switch 33, which is connected in series between the outlets 43 and the power supply, is biased into an open circuit position causing the shutdown of any device plugged into outlets 43.

Figure 4:
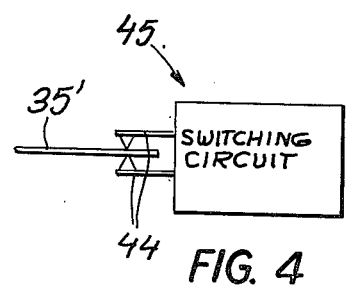
FIG. 4 is a view of another embodiment of an element similar to that shown in FIG. 3B.

Another type of moisture sensing device 45 is shown in FIG. 4 in which a pair of electrodes 44, connected with a switching circuit responsive to changed in electrical conductivity, are in contact with a strip of filter paper 35' which can be positioned in either of the trays 11 or 31 for absorbing spilled liquid which will cause a change in electrical conductivity of the paper.

We claim:
1. A fraction collector comprising:
   a support;
   an upwardly open tray mounted on said support and having a pitched surface;
   electrically operated means on said support for carrying an array of upwardly open vessels successively past a location fixed relative to said support and above said tray;
   a source of liquid mounted on said support;
   a dispensing tip on said support for discharging said liquid into successive vessels at said locations;
   an electrically operated valve interconnecting said source and said tip for controlling the flow of liquid to said vessel;
   liquid-detector means at the bottom of said pitched surface responsive to the presence of liquid thereat; and
   an electric switch operated by said liquid-detector means for deenergizing said valve and said electrically operated means upon the detection of liquid by said liquid-detector means.

2. The apparatus defined in claim 1 wherein said liquid-detector means includes a spring biasing said switch into a nonconductive condition; and
   a moisture-destructible element retaining said switch in a conductive position against the force of said spring.

3. The apparatus defined in claim 2 wherein said destructible element is a strip of filter paper held under tension by said spring and capable of being pulled apart when wetted.

4. The apparatus defined in claim 2 wherein said destructible element is a tube of filter paper held under compression by said spring and adapted to be collapsed when wetted.

* * * * *